United States Patent [19]

Minto

[11] 3,975,097

[45] Aug. 17, 1976

[54] TESTING APPARATUS WHICH MEASURES INDEX OF REFRACTION

[75] Inventor: Wallace Louis Minto, Sarasota, Fla.

[73] Assignee: Sarasota Instruments Inc., Sarasota, Fla.

[22] Filed: Nov. 20, 1974

[21] Appl. No.: 525,540

[52] U.S. Cl. .............................. 356/30; 356/128; 356/209
[51] Int. Cl.² .................. G01N 21/46; G01N 21/48
[58] Field of Search ............... 356/30, 31, 128, 209, 356/212

[56] References Cited
UNITED STATES PATENTS

| 3,245,306 | 4/1966 | Potter et al. .................. 356/209 X |
| 3,483,385 | 12/1969 | Heaslip et al. .................. 356/212 X |
| 3,751,162 | 8/1973 | Long .................................. 356/30 |

OTHER PUBLICATIONS

Bartz et al., *Led Print Analyzer*, IBM Technical Disclosure Bulletin, vol. 14, No. 3, Aug. 1971, p. 887.

Primary Examiner—Eugene La Roche
Attorney, Agent, or Firm—Wolder & Gross

[57] ABSTRACT

An apparatus for measuring the index of refraction of a specimen includes a stage plate having a small exposure opening behind which are located a point source infra-red light emitting diode and a photoresistor. A first lens focusses the LED point source along a first optical axis at the exposure opening on the plane of the specimen receiving face of the stage plate defining a sensing area and a second lens focusses the image on the sensing area along a second optical axis onto the photoresistor. The optical axes form equal angles to the perpendicular to the exposure plane at the center of the sensing area. The light emitting diode and the photoresistor are connected through a common normally open switch to a battery.

7 Claims, 2 Drawing Figures

U.S. Patent   Aug. 17, 1976   3,975,097
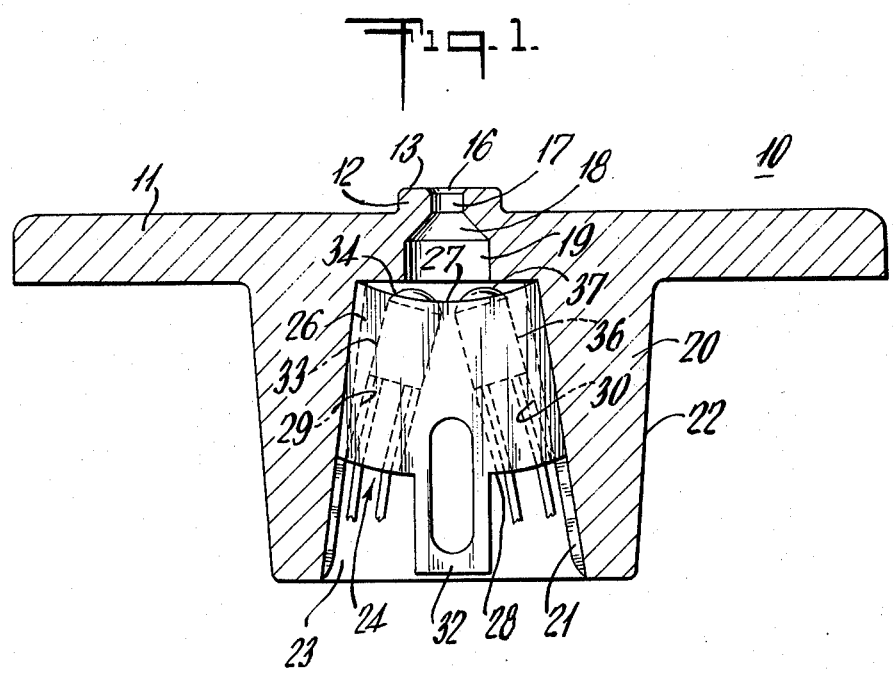
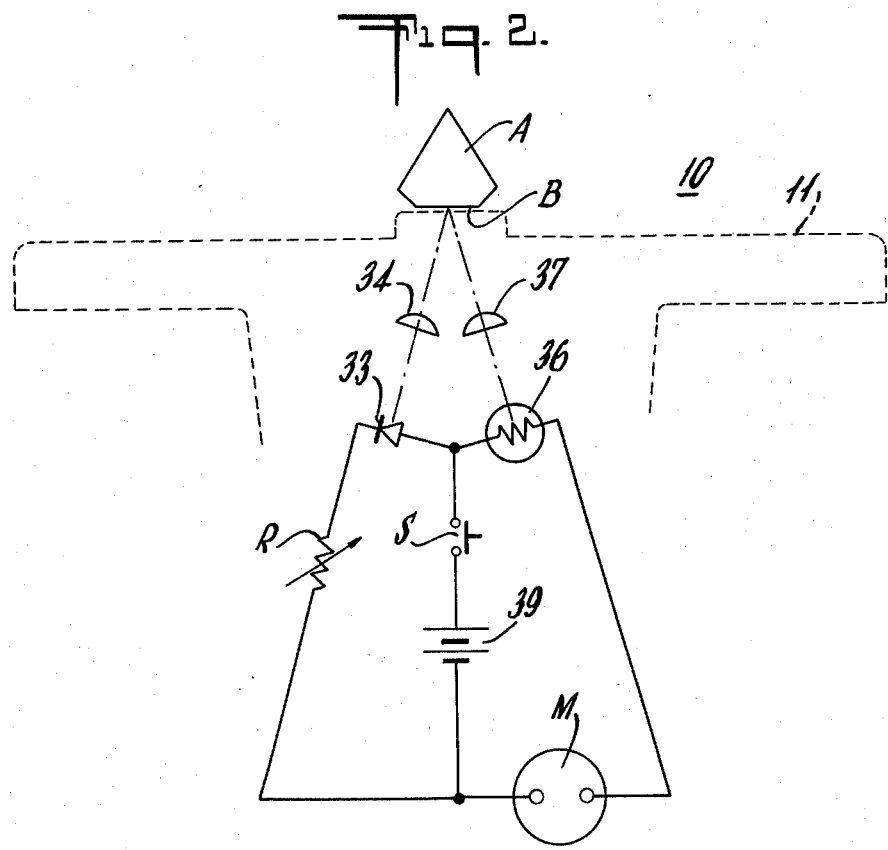

TESTING APPARATUS WHICH MEASURES INDEX OF REFRACTION

BACKGROUND OF THE INVENTION

The present invention relates generally to improvements in methods and apparatus for testing and analyzing materials and it relates particularly to an improved method and apparatus for determining the index of refraction of a material, such method and apparatus being highly useful in identifying minerals such as stones of gem, precious and semi-precious natures.

It is a well known practice in establishing the identity of most gem stones to determine their indices of refraction. However, the instruments heretofore commonly available for the determination of the parameter by gemologists and jewelers have as an upper limit of utility a refractive index of 1.81. This upper limit is well below the refractive index of diamond (2.42) and of most diamond imitations, which range from 1.95 for zircon to 2.65 or more for rutile, and thus these instruments are incapable of differentiating true diamonds from their many less valuable imitations. With the recent advent on the market of many clear synthetic gemstones of high refractive index which have the appearance of diamonds, the need for a rapid and accurate means for differentiating among them has greatly increased to prevent both innocent and fraudulent mistakes as to the nature and value of gems in commerce.

The refractometers available to gemologists and jewelers depended for their operation upon Snell's Law, which states that the relative index of refraction is equal to the ratio of the sine of the angle of incidence to the sine of the angle of refraction when crossing the interface between media of different indices of refraction. In such previous instruments, the refractive index was measured by a determination of the critical angle, that is, the angle at which total reflection at an interface occurs. Because of the method used, such previous instruments are limited by the refractive index of the immersion liquid used on the facet of the gem stone, which must be higher than the index of the gem being tested. The liquid of highest attainable refractive index is a solution of tetraiodoethylene and sulfur in methylene iodide which has a refractive index of 1.81. This liquid is poisonous and highly corrosive and can severely damage the refractometer and even some gemstones if left in contact therewith.

SUMMARY OF THE INVENTION

It is a principal object of the present invention to provide an improved method and apparatus for testing and analyzing materials.

Another object of the present invention is to provide an improved method and apparatus for measuring the index of refraction of a material.

Still another object of the present invention is to provide an improved method and apparatus for identifying materials such as gems, precious and semi-precious stones and other materials of a solid or fluid nature.

A further object of the present invention is to provide an improved method and apparatus of the above nature characterized by their reliability, accuracy, high resolution, speed, simplicity, ruggedness, low cost and great versatility and adaptability.

The above and other objects of the present invention will become apparent from a reading of the following description taken in conjunction with the accompanying drawing which illustrates a preferred embodiment thereof.

The method and apparatus of the present invention do not depend upon the measurement of the critical angle, but instead operates on the principal that, for a gem stone with a polished facet immersed in air, the proportion of light reflected from a beam of light incident on the facet at an angle normal to the facet is a function of the index of refraction of the material which constitutes the polished facet.

Specifically $$\sqrt{R} = \frac{N-1}{N+1}$$

Where $R$ is the proportion of light reflected and $N$ is the index of refraction of the material constituting the polished surface.

However, this principle cannot be used in practice in measuring the refractive index of cut diamonds and other gem stones, since most diamonds and their imitations are transparent crystals which have been deliberately facetted in such a manner that a ray of light impinging normal to the table facet suffers multiple internal reflections within the gem to emerge again through the main table facet, and thus the total amount of light received by any receptor in front of the table facet is a function of the cut of the gem as well as its composition.

In the apparatus of the present invention, this problem is overcome by illuminating the table facet with a sharply converging beam of light which is focussed on the plane of the table facet and is incident thereon at a non-normal fixed angle to that plane. The light receptor or light measuring system also employs a focussing lens which is also focussed in the plane of the table facet and at an angle thereto, which angle is equal to that of the incident rays. By this means, the part of the incident light which enters the transparent gem and is internally reflected is diffused and out of focus to the receptor if it should reemerge from the table facet and only an extremely small proportion of such internally reflected light can emerge at the correct angle to be received by the receptor. Therefore, the light sensing device reacts almost exclusively to that proportion of the incident light which is reflected from the polished surface of the facet of the gem presented to the plane of focus of the light emitter, which is also the plane of focus of the light sensor.

Another problem is that the proportion of light reflected from the surface varies with the wave length of the incident light, and thus ambiguous readings are derived if ordinary white light or the light from an incandescent filament is used. This problem is overcome in the apparatus of the present invention preferably by using a light emitting diode or other source of light radiation which is substantially monochromatic, that is, the light is sharply peaked around some specific wave length or is restricted to a narrow spectral band.

Since the proportion of the light falling on the receptor is thus governed almost solely by the index of refraction of the material comprising the reflective surface, there is no upper limit to the refractive index that can be measured by this method, and it therefore can be used to measure the indices of all known substances.

An advantage of the present method is that no immersion liquids are employed, with their attendant disadvantages and their hazards to unskilled personnel. Another advantage is the ease of employing simple electronic circuitry to sense the amount of light reflected by the gem facet, which permits a simple and unambiguous readout of the refractive index on a digital or conventional or other electrical meter.

A further advantage of the method and apparatus of the present invention is that they may be used to differentiate among various metallic alloys frequently encountered in the jewelry and allied professions. For example, the refractive index of pure copper is about 17.0 while that of pure gold is about 61.0, while various alloys of those two elements have refractive indices proportional to their composition between those extremes. Thus the karat composition of a gold-copper alloy may be determined merely by presenting a polished flat surface of the alloy to the apparatus light focal points.

Similarly, the present method and apparatus permit ready differentiation between platinum, with a refractive index of 12.7 and certain stainless steels of similar appearance and resistance to corrosion which have an index of about 9.0.

Although the improved method and apparatus are employed to great advantage in the jewelry and allied trades, by an obvious suitable modification of the apparatus they have great utility in numerous other applications which deal with solid, liquid or gaseous substances where it would be useful to identify the composition of matter on either a discrete lot or on continuous flow basis. For example, if the focal plane of reflection is adjusted to the plane surface of any liquid, it can furnish information about the composition of that liquid in a widely useful electrical output form. The determination or monitoring of the amount of any solute dissolved in any solvent is thereby permitted in any sample or any process stream. In the latter case, the varying electrical output may be employed for adjusting devices which control or regulate various process parameters to maintain the stream within a desired composition, as is desirable in oil refineries and chemical processing industries. It may be used to determine or control the composition of optical glasses, various plastics, enamels, ceramics, metallic alloys and numerous other technological processes and products where the refractive index is a useful and convenient parameter. The improved apparatus and method are useful in scientific and medical research and testing laboratories to perform functions that are impossible or inconvenient through the use of a conventional refractometer.

A preferred form of the improved apparatus includes:

1. A battery or other source of electrical power which energizes:
2. A light-emitting diode, which provides optical radiation of a peaked wave length from virtually a point source, and
3. A collimating or condensing lens of short focal length to produce a converging beam, which focusses on
4. A small aperture in a plane surface upon which a polished flat face of the specimen being tested is placed. The upper surface of this plane lies at or near the focal point of the lens and at a large angle to the optical axis of the incident light beam, but not at right angles to such axis. The reflected portion of the incident beam is directed to
5. A collimating lens of short focal length which collects the reflected beam and concentrates it upon
6. An electro-optical sensor of the photo-voltaic, photo-resistive or photo-transistor type or other sensor which provides a voltage or current, or other parameter output proportionate to the intensity of light falling upon it. Its output signal is either amplified or directly read by
7. A suitable electrical meter, preferably calibrated directly in refractive index units or some other units which vary with the variation in the index of refraction to provide directly useful information.

Alternatively, the light may be focussed in a ray projecting almost, but not quite vertically downward, whence it is reflected from the surface of a liquid which is plane by reason of the force of gravity operating on it.

In the foregoing illustrations the index of refraction of the specimen is compared with that of air, which is very nearly unity. However, in some instances, such as that of a volatile liquid or a process stream in rapid movement, it may be advantageous to direct the incident light beam through a window of suitable known refractive index onto its interface with the liquid or gas being examined. In that case, the light reflected from the plane interface is proportional to the difference between the refractive index of the material comprising the window and the fluid under test.

The improved method and apparatus are highly reliable and accurate and of great resolution. They are easy, simple, rapid and convenient to use and are of great versatility and adaptability. The apparatus is rugged, compact and of low cost.

BRIEF DESCRIPTION OF THE DRAWING

FIG. 1 is a vertical medial sectional view of the sensing section of an apparatus embodying the present invention; and FIG. 2 is a schematic view thereof and the associated circuit network.

DESCRIPTION OF THE PREFERRED EMBODIMENT

Referring now to the drawing which illustrates a preferred embodiment of the present invention as applied to the indentification by refractive index measurement of a facetted stone A, defining a specimen, which has a polished flat planar face B, such as a cut stone which may be of gem, precious or semi-precious quality, natural, artificial or synthetic, the reference numeral 10 generally designates a specimen or object positioning stage which may be formed of metal or a synthetic polymeric resin or other suitable material.

The stage 10 includes a circular top plate 11 having a slightly raised centrally located, circular raised portion 12 defining a specimen positioning section, the raised portion 12 having a horizontal flat planar top face 13. The concentric raised portion 12 and plate 11 have a central coaxial vertical bore 14, including a shallow frustoconical top section 16 having an upwardly, outwardly flaring face, whose lower edge joins a depending cylindrical bore section 17. An intermediate frustoconical bore section 18 with a downwardly, outwardly flaring face depends from bore section 17 and terminates in a depending cylindrical bore section 19 which extends to the bottom face of plate 11.

Integrally formed with the plate 11 and depending vertically therefrom is a collar section 20 having a frustoconical inside face 21 extending from the bottom of collar 20 to the underface of plate 11 at a circle of greater radius than and concentric with the bottom of bore section 19. The outside face 22 of collar 20 tapers slightly outwardly, upwardly.

Positioned in the well 23 delineated by the collar inside wall 21 is a sensing unit or assembly 24 which includes a polymeric resin block 26 having a concave cylindrical top face 27, a convex cylindrical bottom face 28 and upwardly converging side faces mating the collar inside face 21. The block 26 is tightly wedged into and affixed to the face of well 23 with the upper edges of concave face 27 engaging the underface of plate 11 at its intersection with face 21. A pair of diametrically opposed upwardly converging bores 29 and 30 are formed in block 26, the axes of the bores intersecting at the axis of bore section 16 at the plane of surface 13. An apertured finger 32 medially depends from block 26.

A light emitting diode 33 having a vertical point radiation source, and preferably of the infra-red emitting type, although sharply spectral peaked or monochromatic types of other wave lengths may be employed, coaxially nests in the bore 29 and is firmly affixed therein. The light emitting diode 33 includes a short focal length lens 34 registering with the top opening of bore 29 and so positioned as to focus an image of the diode emission point source onto the plane of surface 13 at the axis of bore section 16.

A photo-resistor member 36, or any other photo-responsive member which is sensitive to the emission of light emitting diode 33, nests in the bore 30 and is firmly affixed therein. The photo-resistor member 36 includes a lens 37 similar to lens 34 and positioned and oriented to focus the image of the point radiation source on the plane of surface 13 onto the photo-sensitive element of photo-resistor member 36. The optical axes of the lenses 34 and 37 form equal angles between ½° and 45° to the normal to the plane of surface and the inside faces of bore 14, concave face 27 and the underface of plate 11 in well 23 are non-reflective and highly absorbent of the radiation emitted by diode 33.

One terminal lead of light emitting diode 33 is connected through an adjustable calibrating resistor R to a first pole of an energizing battery 39 and the other terminal lead thereof is connected through a normally open push button switch S to the second pole of battery 39. One terminal lead of photo-resistor 36 is connected through a sensitive current meter to the battery first pole and the other terminal lead thereof is connected through switch to the battery second pole. The meter M is advantageously calibrated by index of refraction values, although other designations may be employed. Further, the meter M is provided with a needle zero setting adjustment, advantageously of the mechanical type.

In employing the improved apparatus, a specimen, for example a facetted gem or other stone, having a polished flat face or facet B is positioned so that the facet B rests on and is coplanar with face 13. The switch S is then closed to energize the light emitting diode 33, whose radiation is sharply focussed by lens 34 on the exposed face of facet B, the image of the radiation source preferably being slightly or somewhat larger than the area of the window of bore section 16. The radiation reflected by facet B is focussed by lens 37 onto photo-resistor 36 and the intensity of the radiation incident on photo-resistor 36 varies the resistance thereof which varies the current through meter M to provide a reading which is an indication of or measurement of the index of refraction of the specimen A. The measured index of refraction, in turn, identifies the material of the specimen A. The switch S is released to its open position upon noting the reading of the meter M.

The apparatus may be calibrated or standardized by positioning one or more standard specimens A of known refractive indices on the stage, closing switch S and adjusting resistor R and the meter zero adjustment so that the meter provides readings corresponding to the refractive indices of the standardizing specimens.

While there has been described and illustrated a preferred embodiment of the present invention, it is apparent that numerous alterations, omissions and additions may be made without departing from the spirit thereof.

I claim:

1. An apparatus for measuring the reflectivity of a surface of a material as an indication of the index of refraction of the material comprising stage means for locating a specimen with a face thereof at a sensing position in a predetermined plane, means including an infra-red light emitting diode for projecting a substantially monochromatic beam of infra-red light in a narrow spectral band onto said specimen face at a predetermined first angle to the normal to said plane, an infra-red light sensitive element exposed to the infra-red light beam reflected by the specimen face and means for measuring a parameter of said infra-red light sensitive element responsive to the amount of said infra-red light incident therein as an indication of the index of refraction of said specimen.

2. The apparatus of claim 1 wherein said beam projecting means comprises a condensing first lens between said diode and said plane focussing the light emitting face of said diode onto said predetermined plane at said sensing position.

3. The apparatus of claim 2 wherein said light sensitive element comprises a photo-conductor.

4. The apparatus of claim 3 comprising a second lens disposed between said sensing position and said photo-conductor and focussing the beam reflected by the specimen face onto said photo-conductor.

5. The apparatus of claim 4 wherein the angles between the normal to said plane and the optical axes of said first and second lenses are substantially equal.

6. The apparatus of claim 5 wherein said angles are between 0.5° and 45°.

7. The method of determining the index of refraction of a material as indicated by the reflectivity of a face thereof comprising directing a confined beam of a light emitting diode derived substantially monochromatic infra-red light in a narrow spectral band at a restricted sensing area on a specular substantially planar face of said material at an angle of between 0.5° and 45° to the normal to said face and measuring the relative amount of said beam of infra-red light reflected by said face as an indication of said index of refraction.

* * * * *